United States Patent [19]
Seed et al.

[11] Patent Number: 5,925,657
[45] Date of Patent: Jul. 20, 1999

[54] USE OF PPARγ AGONISTS FOR INHIBITION OF INFLAMMATORY CYTOKINE PRODUCTION

[75] Inventors: Brian Seed; Chengyu Jiang, both of Boston, Mass.

[73] Assignee: The General Hospital Corporation, Boston, Mass.

[21] Appl. No.: 08/878,406

[22] Filed: Jun. 18, 1997

[51] Int. Cl.$^6$ .................... A01N 43/78; A61K 31/425
[52] U.S. Cl. .................... 514/369; 514/370; 514/340; 514/366; 514/365
[58] Field of Search .................... 514/369, 370, 514/340, 366, 365

[56] References Cited

U.S. PATENT DOCUMENTS 5,594,015  1/1997  Kurtz et al. .................... 514/369

OTHER PUBLICATIONS

Chemical Abstracts AN 1997:653205, Peraldi et al. Oct. 1997.
Chemical Abstracts AN 1994:692489, Ohsumi et al., Jan. 1994.
Chawla et al., "Peroxisome proliferator–activated receptor (PPAR) γ:adipose–predominant expression and induction early in adipocyte differentiation," Endocrinol. 135:798–800, 1994.
Forman et al., "15–deoxy–$\Delta^{12, 14}$–prostaglandin J$_2$ is a ligand for the adipocyte determination factor PPARγ," Cell 83:803–812, 1995.
Hu et al., "Transdifferentiation of myoblasts by the adipogenic transcription factors PPARγ and C/EBPα," Proc. Natl. Acad. Sci. USA 92:9856–9860, 1995.
Kliewer et al., "A rostaglandin J$_2$ metabolite binds peroxisome proliferator–activated receptor γ and promotes adipocyte differentiation," Cell 83:813–819, 1995.
Lehmann et al., "An antidiabetic thiazolidinedione is a high affinity ligand for peroxisome proliferator–activated receptor γ (PPARγ)," J. Biol Chem. 270:12953–12956, 1995.
Lehmann et al., "Peroxisome proliferator–activated receptors α and γ are activated by indomethacin and other non–steroidal andti–inflammatory drugs," J. Biol. Chem. 272:3406–3410, 1997.
Tontonoz et al., "mPPARγ2: tissue–specific regulator of an adipocyte enhancer," Genes Dev. 8:1224–1234, 1994.
Tontonoz et al., "Stimulation of adipogenesis in fibroblasts by PPARγ2, a lipid–avtivated transcription factor," Cell 79:1147–1156, 1994.
Peraldi et al., "Thiazolidinediones block tumor necrosis factor–α–induced inhibition of insulin signaling," J. Clin invest, 100:1863–1869, 1997.
Ohsumi et al., "Troglitazone prevents the inhibitory effects of inflammatory cytokines in insulin–induced adipocyte differentiation in 3T3–L1 cells," Endocrinology, 135:2279–2282, 1994.

*Primary Examiner*—Keith D. MacMillan
*Attorney, Agent, or Firm*—Clark & Elbing LLP

[57] ABSTRACT

Disclosed herein are methods for reducing or preventing cytokine production associated with an inflammatory response, involving administering to a mammal a therapeutically-effective amount of a thiazolidinedione PPARγ agonist.

12 Claims, 6 Drawing Sheets

USE OF PPARγ AGONISTS FOR INHIBITION OF INFLAMMATORY CYTOKINE PRODUCTION

BACKGROUND OF THE INVENTION

In general, this invention relates to the use of thiazolidinedione PPARγ agonists for inflammatory conditions.

Recent studies have implicated the peroxisome proliferator-activated receptor gamma (PPARγ), a member of the nuclear hormone receptor family of transcription factors, in the regulation of adipogenesis. Expression of PPARγ is one of the earliest events in adipocyte differentiation (Chawla et al., Endocrinol. 135:798–800 (1994) and Tontonoz et al., Genes Dev. 8:1224–1234 (1994)), and ectopic expression of PPARγ in fibroblast and myoblast cell lines causes transfected cells to undergo differentiation into adipocytes (Tontonoz and Spiegelman, Cell 79:1147–1156 (1994) and Hu et al., Proc. Natl. Acad. Sci. USA 92:9856–9860 (1995)). A number of agents promote differentiation of fibroblast lines into adipocytes, and a unifying observation appears to be that many such agents exert their effect through PPARγ (Lehmann et al., J. Biol. Chem. 270:12953–12956 (1995); Kliewer et al., Cell 83:813–819 (1995); Forman et al., Cell 83:803–812 (1995); and Lehmann et al., J. Biol. Chem. 272:3406–3410 (1997)). Compounds with activity in the adipocyte differentiation assay form a diverse group, including several prostanoids, of which 15-deoxy-$\Delta^{12,14}$-prostaglandin $J_2$ (15d-$PGJ_2$) is the most potent (Kliewer et al., Cell 83:813–819 (1995) and Forman et al., Cell 83:803–812 (1995)), members of a new class of oral antidiabetic agents, the thiazolidinediones (Lehmann et al., J. Biol. Chem. 270:12953–12956 (1995)), and a number of non-steroidal anti-inflammatory drugs (Lehmann et al., J. Biol. Chem. 272:3406–3410 (1997)).

SUMMARY OF THE INVENTION

In a first aspect, the invention features a method for reducing or preventing inflammatory cytokine production associated with rheumatoid arthritis in a mammal, involving administering to the mammal a thiazolidinedione PPARγ agonist in an amount which is sufficient to produce a 50% inhibition of cytokine production in a mammalian monocyte culture.

In a second aspect, the invention features a method for reducing or preventing inflammatory cytokine production associated with inflammatory bowel disease in a mammal, involving administering to the mammal a therapeutically-effective amount of a thiazolidinedione PPARγ agonist.

In a third aspect, the invention features a method for reducing or preventing inflammatory cytokine production associated with an immunodeficiency syndrome in a mammal, involving administering to the mammal a therapeutically-effective amount of a thiazolidinedione PPARγ agonist.

In a fourth aspect, the invention features a method for reducing or preventing inflammatory cytokine production associated with multiple sclerosis in a mammal, involving administering to the mammal a therapeutically-effective amount of a thiazolidinedione PPARγ agonist.

In a fifth aspect, the invention features a method for reducing or preventing inflammatory cytokine production associated with cachexia (for example, resulting from a neoplasia or chronic infectious disease) in a mammal, involving administering to the mammal a therapeutically-effective amount of a thiazolidinedione PPARγ agonist.

In preferred embodiments of each of the above aspects, the thiazolidinedione is troglitazone; the cytokine is TNFα, IL-1β, or IL-6; the cytokine is produced by a monocyte; the thiazolidinedione PPARγ agonist is administered orally; and the thiazolidinedione PPARγ agonist is administered in an amount which is sufficient to produce a 50% inhibition of cytokine production in a mammalian monocyte culture.

As used herein, by "reducing or preventing" is meant effecting a decrease in the amount of a cytokine produced in response to an inflammatory stimulus. This term also includes inhibition of initial inflammatory cytokine induction.

By an "inflammatory cytokine" is meant a protein synthesized by an immune cell, for example, a monocyte, in response to an inflammatory stimulus. Inflammatory cytokines include, without limitation, TNFβ, TNF-β, IL-1α, IL-1β, IL-6, interferons, and agents that mimic the actions of these compounds.

By a "PPARγ agonist" is meant any compound that increases or mimics the activity of a peroxisome proliferator-activated receptor gamma.

By a "thiazolidinedione" is meant a compound which has a substituted aryl moiety attached to a thiazolidinedione nucleus. This term includes, without limitation, any compound described in Kurtz et al., U.S. Pat. No. 5,594,015, hereby incorporated by reference.

By a "neoplasia" is meant any abnormal tissue that grows by cellular proliferation more rapidly than normal, continues to grow after the stimulus that initiated the new growth has ceased, or shows partial or complete lack of structural organization and functional coordination with normal, surrounding tissue. Such a neoplasia is typically malignant.

By a "chronic infectious disease" is meant a condition characterized by an interruption, cessation, or disorder of a body function, system, or organ that is caused by the presence or activity of a pathogenic organism and that continues in duration over a time period of at least 30 days, more typically, at least 60 days, and, most typically, at least 90 days.

By a "monocyte" is meant any hematopoietic cell of the monocyte lineage, including monocytes and macrophages.

The invention described herein provides a new approach to the treatment of inflammatory diseases through the use of thiazolidinedione PPARγ agonists, which applicants have shown inhibit inflammatory cytokine induction. In addition, as a result of applicants' discovery that such agonists possess this inhibitory activity in mammalian monocyte culture, the invention also enables the determination of appropriate dosages of thiazolidinedione PPARγ agonists for human administration and for treatment of such diseases or conditions.

Other features and advantages of the invention will be apparent from the following detailed description thereof, and from the claims.

BRIEF DESCRIPTION OF THE DRAWINGS

The drawings are first briefly described.

DETAILED DESCRIPTION

Described herein are experiments demonstrating that PPARγ agonists suppress monocyte elaboration of inflammatory cytokines (including TNFα, IL-1β, and IL-6) at agonist concentrations comparable to those found effective for the promotion of adipogenesis. These PPARγ agonists include thiazolidinediones (for example, troglitazone), PGJ$_2$ prostanoids, and nonsteroidal anti-inflammatory drugs (NSAIDs). In one particular example, troglitazone inhibition of cytokine production by freshly explanted monocytes in culture took place within the range of drug plasma concentrations observed following typical oral administration of this compound in humans. These experiments are now described in more detail.

Inhibition of Inflammatory Cytokine Production by PPARγ Agonists

To assay for inflammatory cytokine production, human peripheral blood monocytes were isolated from freshly collected buffy coat preparations of whole human blood. The mononuclear cell fraction was prepared by dilution with an equal volume of phosphate buffered saline (PBS) at room temperature, layered over Ficoll-Hypaque solution (3 ml Ficoll-Hypaque per 10 ml blood/PBS mixture), and centrifuged for 30 minutes in a Sorvall RT6000 centrifuge at 900×g. The mononuclear cell layer was transferred to a fresh tube, mixed with 3 volumes of PBS, and centrifuged 10 minutes at 400×g. The supernatant was then removed, and the dilution and centrifugation were repeated three times. Mononuclear cells were resuspended in RPMI medium 1640 (Life Technologies, Gaithersburg, Md.), counted, and diluted to $5 \times 10^6$ cells per ml. One ml was then transferred to each well of 24 well tissue culture plates and incubated for 1 hour in a 37° C., 5% $CO_2$ humidified incubator. The nonadherent lymphocytes were removed, and the monocytes were washed once with 1X PBS before adding 1 ml fresh RPMI medium 1640 with 10% fetal bovine serum. Experiments were initiated the same day blood was collected.

Cytokine synthesis was induced and inhibition of induction examined by treatment of monocytes which had been incubated in fresh medium for 2 to 5 hours with inducers and candidate inhibitors of induction. Medium was harvested from triplicate wells 18 to 20 hours after addition of the test compounds. Supernatant concentrations of human TNFα, IL-6, and IL-1β were measured by ELISA assay using protocols supplied by the manufacturers (Immunotech, Westbrook, Me. and Endogen, Boston, Mass.).

Figure 1:
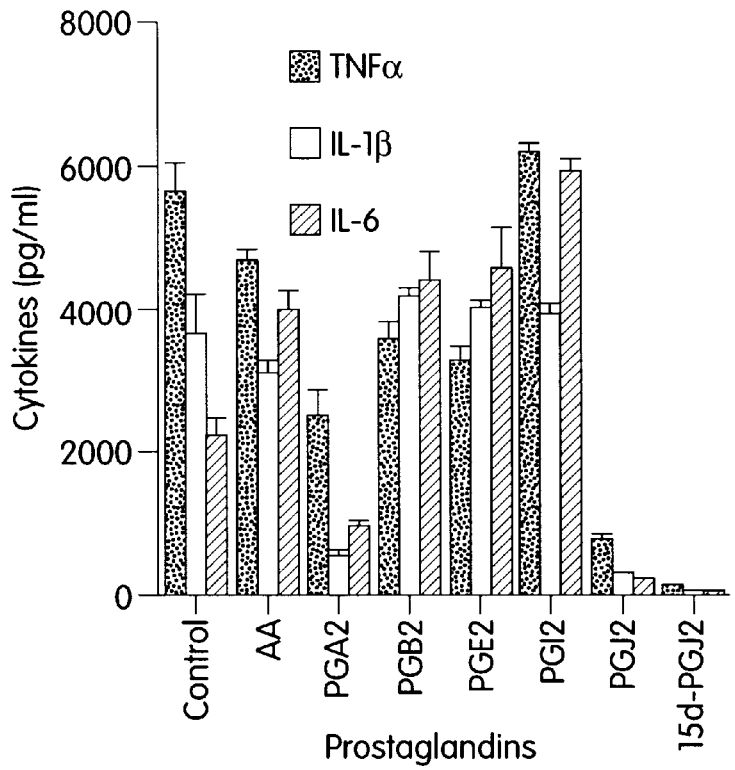
FIG. 1 is a graph illustrating the effects of prostaglandin metabolites on phorbol ester induction of inflammatory cytokines in human monocytes. Freshly prepared human monocytes were incubated in medium containing 25 nM phorbol ester (PMA) and either vehicle only (DMSO—"Control"), 10 μM arachidonic acid ("AA"), or 10 μM of one of the following prostanoids: prostaglandin $A_2$ ("PGA2"), prostaglandin $B_2$ ("PGB2"), prostaglandin $E_2$ ("PGE2"), prostaglandin $I_2$/6-keto prostaglandin $F_{1\alpha}$ ("PGI2"), prostaglandin $J_2$ ("PGJ2"), and 15-deoxy $\Delta^{12,14}$-prostaglandin $J_2$ ("15d-PGJ2"). The concentrations of TNFα, IL-6, and IL-1β which were released into the medium was determined by ELISA assay of culture supernatants. Shown in FIG. 1 are the mean ± standard deviation values of triplicate determinations.
Figure 2:
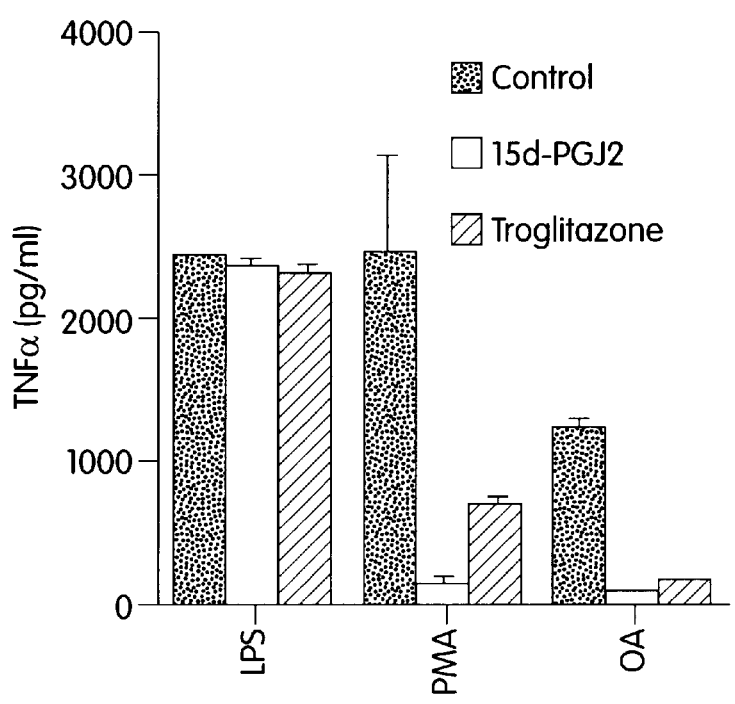
FIG. 2 is a graph illustrating the effects of the PPARγ agonists, troglitazone and 15-PGJ$_2$, on induction of TNFα by lipopolysaccharide (LPS), phorbol ester (PMA), and okadaic acid (OA). Freshly prepared human monocytes were coincubated with either 30 μM troglitazone or 10 μM 15d-PGJ$_2$ in medium containing 1 ng/ml LPS, 25 nM PMA, or 50 nM OA. TNFα released into the medium was measured by ELISA. Control cultures were incubated with inducer and vehicle (DMSO) only. Shown are the mean ± standard deviation values of triplicate determinations.

FIG. 1 shows that cytokine synthesis induced by phorbol myristyl acetate (PMA) was inhibited by prostanoids in the $PGJ_2$ family, and that other prostaglandins had relatively little effect. A similar pattern of activity has been reported for prostaglandins which are known to exert their biological activity at least in part through activation of PPARγ. Consistent with this observation, the structurally dissimilar PPARγ agonist troglitazone was found to inhibit PMA-induced TNFα synthesis. This result is shown in FIG. 2.

Cells of the monocyte/macrophage lineage can be induced to secrete inflammatory cytokines following exposure to a variety of exogenous agents, including phorbol esters, okadaic acid (OA), bacterial lipopolysaccharide, and various synergistic combinations of cytokines and receptor-mediated priming. FIG. 2 shows that lipopolysaccharide-induced cytokine synthesis was largely refractory to the effects of 15d-$PGJ_2$ and troglitazone, whereas phorbol ester and okadaic acid-induced cytokine synthesis was susceptible to their action.

Figure 3:
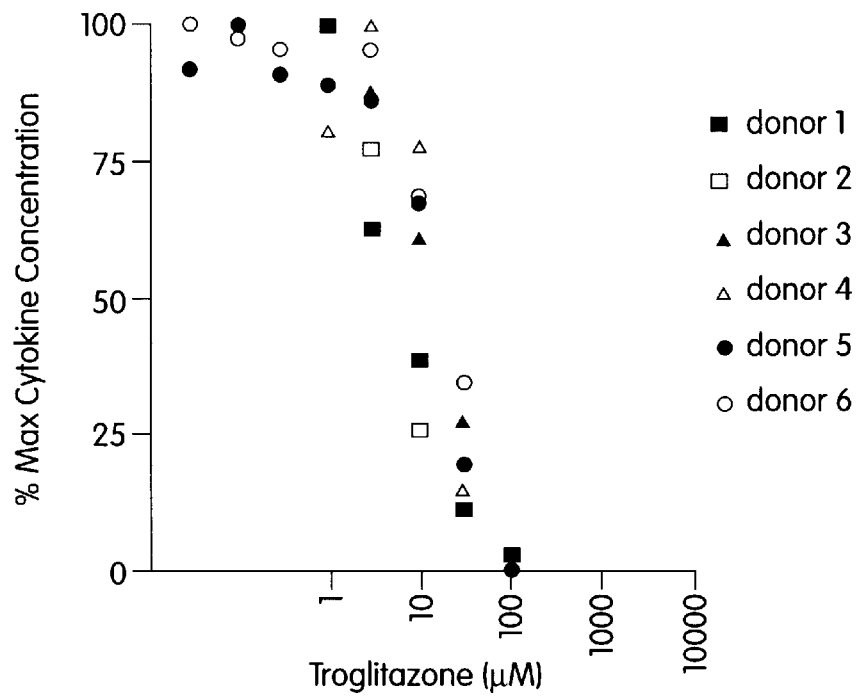
FIG. 3 is a graph illustrating the dose response for inhibition by troglitazone of PMA-induced cytokine synthesis in monocytes prepared from multiple donors. Human monocyte cultures initiated from six unrelated donors were treated with 25 nM PMA and different concentrations of troglitazone. The concentration (in pg/ml) of TNFα released in the medium was measured by ELISA assay. Shown are the means of triplicate determinations, displayed as the percent of maximum cytokine concentration recorded. Standard deviations are not diplayed to preserve clarity.
Figure 4:
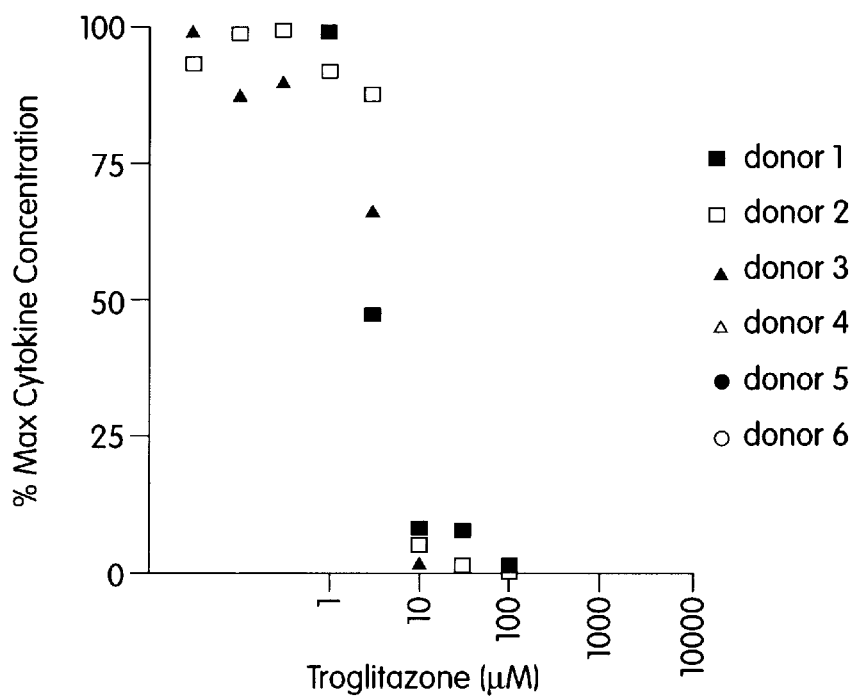
FIG. 4 is a graph illustrating the dose response for inhibition by troglitazone of PMA-induced cytokine synthesis in monocytes prepared from multiple donors. Human monocyte cultures initiated from six unrelated donors were treated with 25 nM PMA and different concentrations of troglitazone. The concentration (in pg/ml) of IL-6 released in the medium was measured by ELISA assay. Shown are the means of triplicate determinations, displayed as the percent of maximum cytokine concentration recorded. Standard deviations are not diplayed to preserve clarity.
Figure 5:
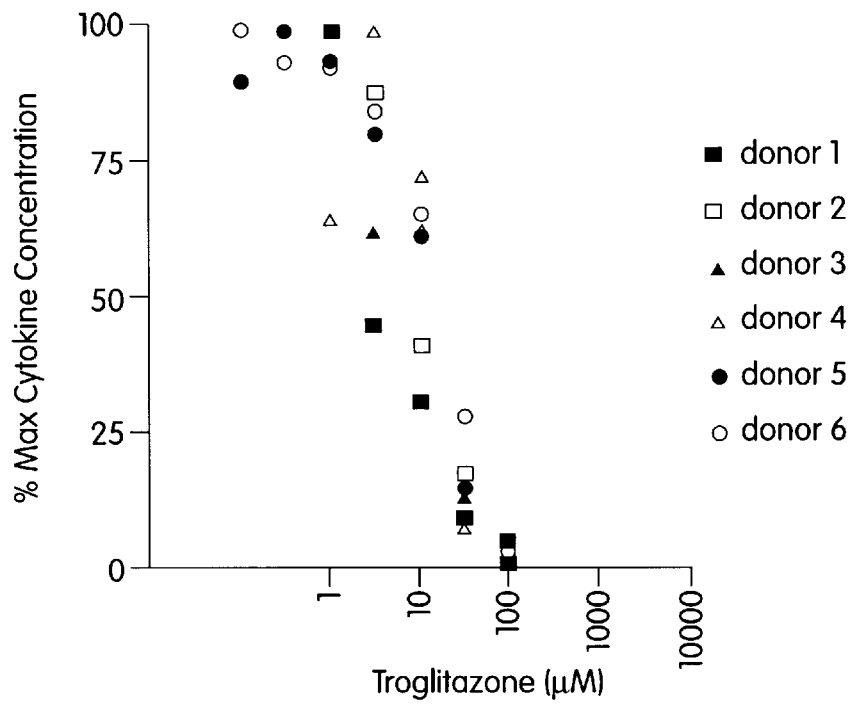
FIG. 5 is a graph illustrating the dose response for inhibition by troglitazone of PMA-induced cytokine synthesis in monocytes prepared from multiple donors. Human monocyte cultures initiated from six unrelated donors were treated with 25 nM PMA and different concentrations of troglitazone. The concentration (in pg/ml) of IL-1β released in the medium was measured by ELISA assay. Shown are the means of triplicate determinations, displayed as the percent of maximum cytokine concentration recorded. Standard deviations are not diplayed to preserve clarity.
Figure 6:
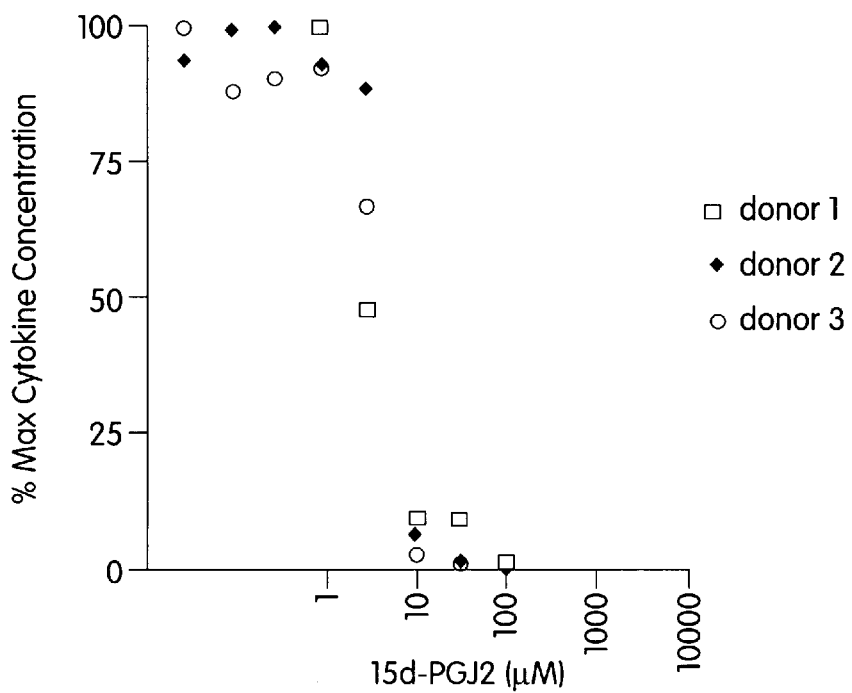
FIG. 6 is a graph illustrating the dose response for inhibition by 15d-PGJ$_2$ of PMA-induced cytokine synthesis in monocytes prepared from multiple donors. Human monocyte cultures initiated from six unrelated donors were treated with 25 nM PMA and different concentrations of 15d-PGJ$_2$. The concentration (in pg/ml) of TNFα released in the medium was measured by ELISA assay. Shown are the means of triplicate determinations, displayed as the percent of maximum cytokine concentration recorded. Standard deviations are not diplayed to preserve clarity.
Figure 7:
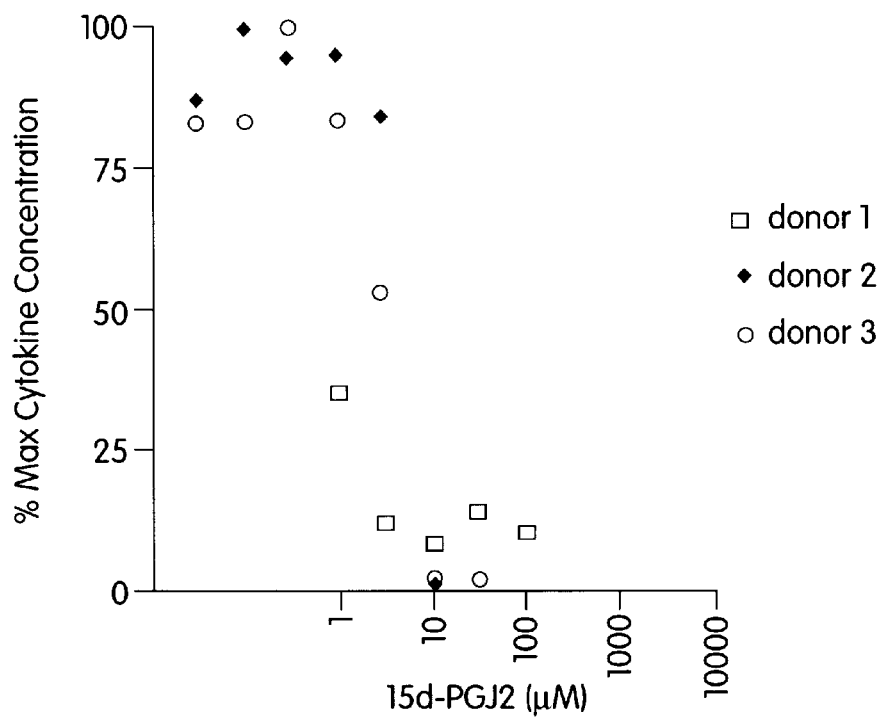
FIG. 7 is a graph illustrating the dose response for inhibition by 15d-PGJ$_2$ of PMA-induced cytokine synthesis in monocytes prepared from multiple donors. Human monocyte cultures initiated from six unrelated donors were treated with 25 nM PMA and different concentrations of 15d-PGJ$_2$. The concentration (in pg/ml) of IL-6 released in the medium was measured by ELISA assay. Shown are the means of triplicate determinations, displayed as the percent of maximum cytokine concentration recorded. Standard deviations are not diplayed to preserve clarity.
Figure 8:
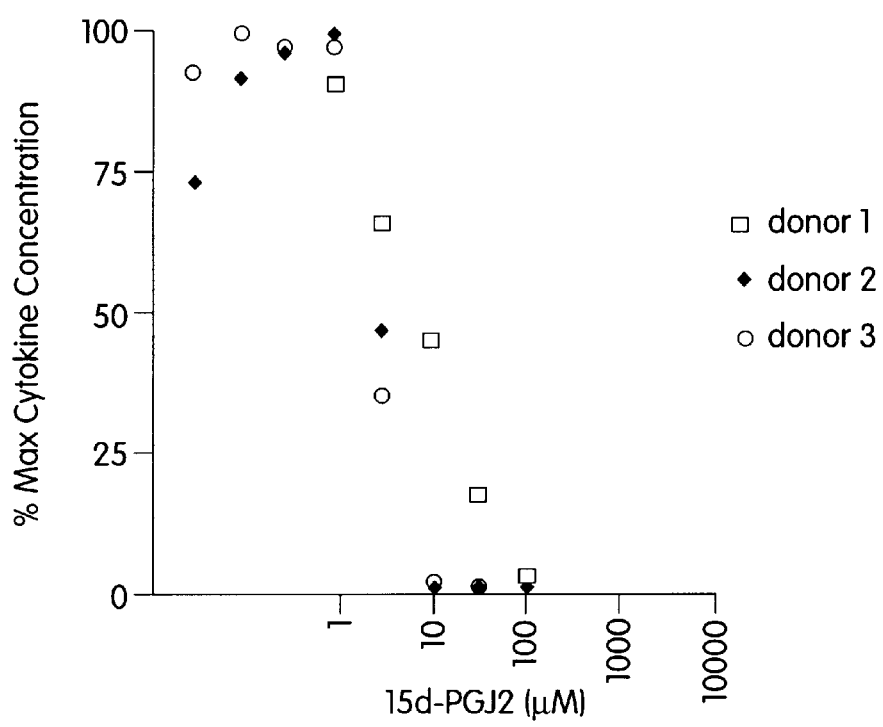
FIG. 8 is a graph illustrating the dose response for inhibition by 15d-PGJ$_2$ of PMA-induced cytokine synthesis in monocytes prepared from multiple donors. Human monocyte cultures initiated from six unrelated donors were treated with 25 nM PMA and different concentrations of 15d-PGJ$_2$. The concentration (in pg/ml) of IL-1β released in the medium was measured by ELISA assay. Shown are the means of triplicate determinations, displayed as the percent of maximum cytokine concentration recorded. Standard deviations are not diplayed to preserve clarity.

To establish the range of concentrations over which 15d-$PGJ_2$ and troglitazone were effective, dose titrations of PMA- and OA-induced cytokine synthesis were performed with monocytes prepared from several unrelated donors. FIGS. 3–5 show that the half-maximal concentration for troglitazone inhibition of PMA-induced cytokine synthesis, PMA IC50, fell in the range of 6 to 18 mM for TNFα, 3 to 20 mM for IL-1β, and 8 to 25 mM for IL-6. As shown in FIGS. 6–8, comparable values for the half-maximal concentration for 15d-$PGJ_2$ inhibition of PMA-induced synthesis were also observed, in particular, between 3 to 7 mM for TNFα, 2 to 10 mM for IL-1β, and 0.8 to 4 mM for IL-6. The close correspondence between IC50 values for the different cytokines suggests a common mechanism of action. The fact that these values fell within the range of concentrations that had previously been reported to be necessary for efficient induction of adipocyte differentiation in vitro (Lehmann et al., J. Biol. Chem. 270:12953–12956 (1995); Kliewer et al., Cell 83:813–819 (1995); and Forman et al., Cell 83:803–812 (1995)) suggests that cytokine inhibition and adipogenesis share a related regulatory circuit mediated by PPARγ.

Figure 9:
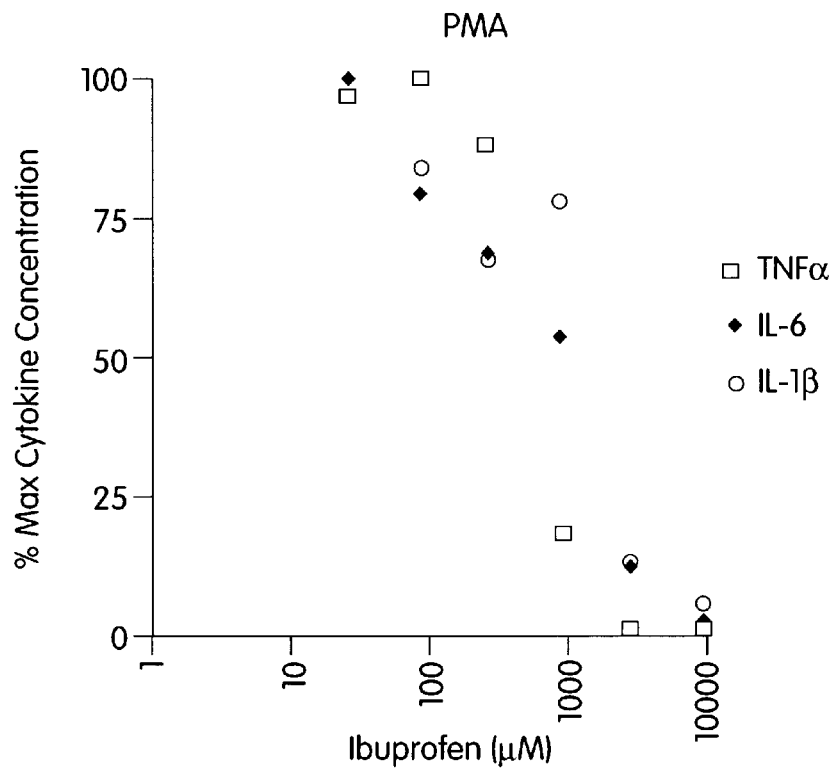
FIG. 9 is a graph illustrating that NSAIDs that act on PPARγ block production of inflammatory cytokines. Human monocyte cultures were treated with 25 nM PMA and different concentrations of ibuprofen. Shown are the means of triplicate determinations, displayed as the percent of maximum cytokine concentration recorded.
Figure 10:
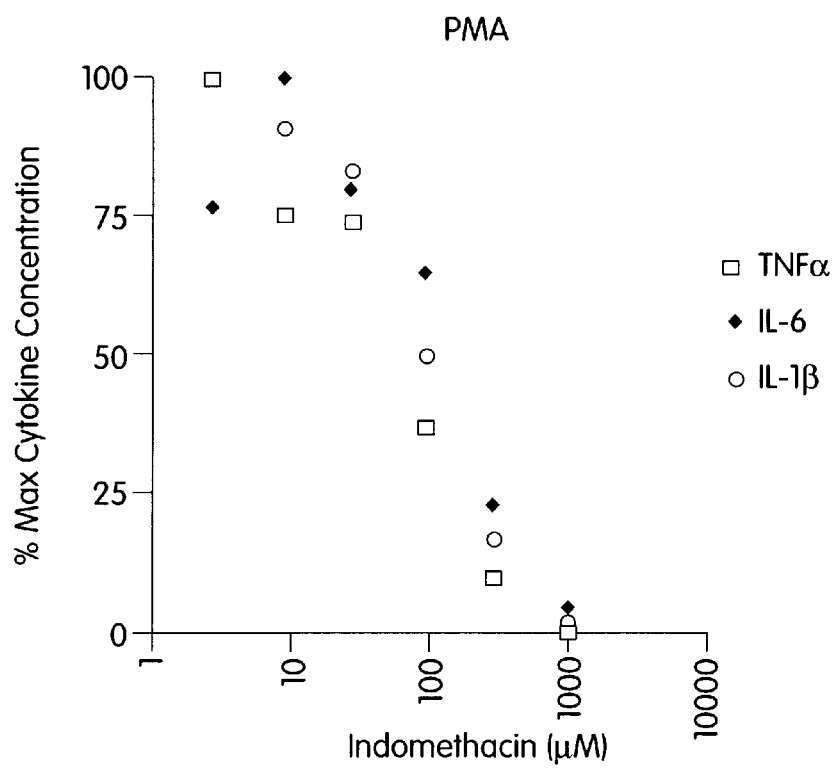
FIG. 10 is a graph illustrating that NSAIDs that act on PPARγ block production of inflammatory cytokines. Human monocyte cultures were treated with 25 nM PMA and different concentrations of indomethacin. Shown are the means of triplicate determinations, displayed as the percent of maximum cytokine concentration recorded.
Figure 11:
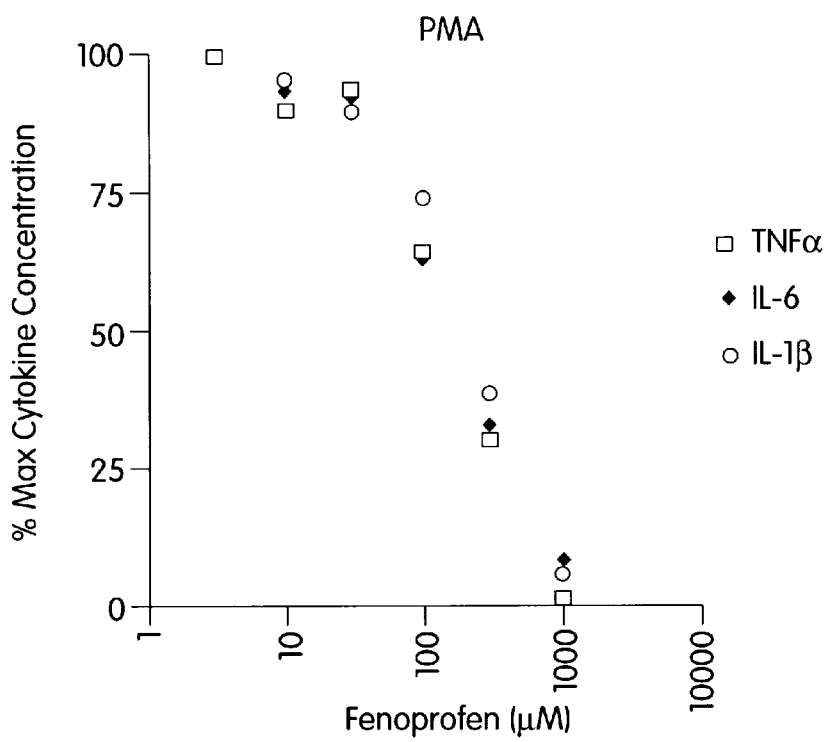
FIG. 11 is a graph illustrating that NSAIDs that act on PPARγ block production of inflammatory cytokines. Human monocyte cultures were treated with 25 nM PMA and different concentrations of fenoprofen. Shown are the means of triplicate determinations, displayed as the percent of maximum cytokine concentration recorded.
Figure 12:
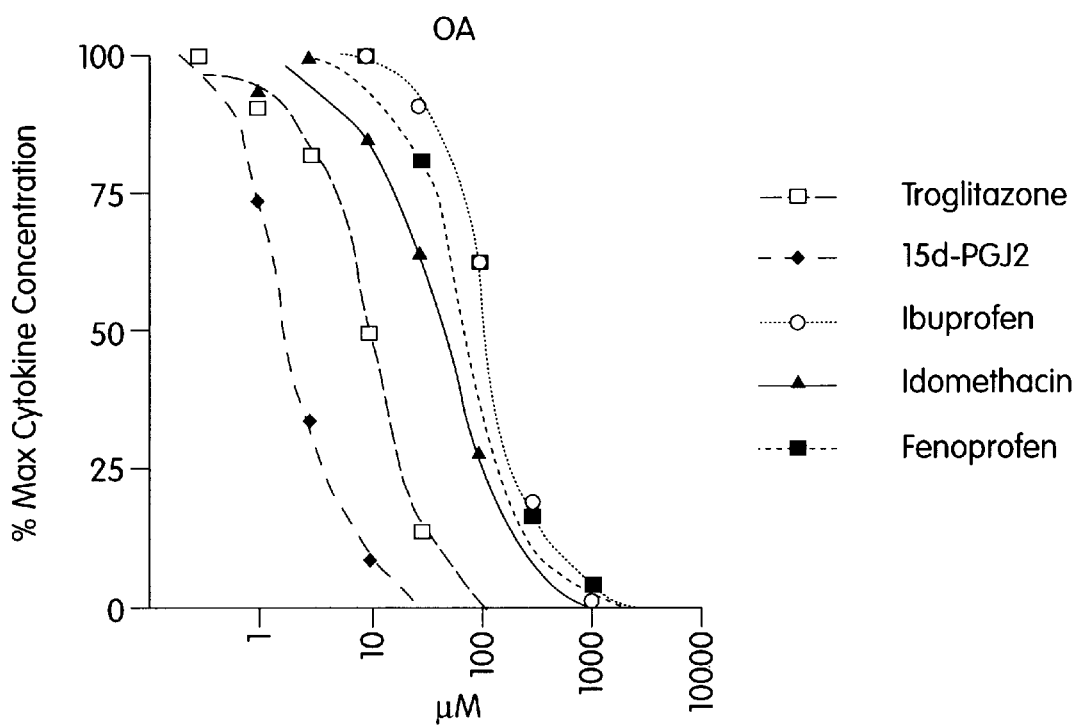
FIG. 12 is a graph illustrating the dose response of inhibition of TNFα production elicited by okadaic acid. Monocyte cultures were induced with okadaic acid in the presence of PPARγ agonists at the indicated concentrations. The PPARγ agonists tested are shown in this figure as follows: troglitazone, open squares; 15d-PGJ$_2$, closed diamonds; ibuprofen, open circles; indomethacin, closed triangles; and fenoprofen, open squares. Shown are the means of triplicate determinations, displayed as the percent of maximum cytokine concentration recorded.

Recently it has been reported that several nonsteroidal anti-inflammatory drugs (NSAIDs), including indomethacin, ibuprofen, and fenoprofen, have PPARγ agonist activities at high concentrations (Lehmann et al., J. Biol. Chem. 272:3406–3410 (1997)). These compounds were tested for their ability to inhibit inflammatory cytokine production induced by phorbol ester. FIGS. 9–11 show that all three agents inhibited PMA-induced cytokine synthesis with essentially cytokine-independent dose response characteristics. The PMA IC50's for inhibition of TNFα synthesis by indomethacin, fenoprofen, and ibuprofen were approximately 40, 180, and 550 mM, respectively (FIGS. 9–11 and data not shown); these values agreed well with the potency and rank order of the same agents in the adipogenesis assay (Lehmann et al., J. Biol. Chem. 272:3406–3410 (1997)). Similar experiments using okadaic acid as an inducer (FIG. 12) gave the same rank order for efficacy, 15d-$PGJ_2$>troglitazone>indomethacin>fenoprofen>ibuprofen, with approximate IC50's of 2, 10, 60, 100, and 200 mM, respectively. High dose NSAID therapy is expected to produce plasma concentrations of up to 10 mM for indomethacin, 300 mM for ibuprofen, and 250 mM for fenoprofen (ASHP.AHFS Drug Information 97:1495–1514 (1997)). These results again indicated that PPARγ agonists were useful for inhibiting inflammatory cytokines, and are therefore useful for the treatment of inflammatory disorders.

The thiazolidinedione oral antidiabetic drugs are a class of pharmacological agents with the potential to decrease insulin need and retard progression to insulin dependence in adult diabetics. As adipogenic mediators, thiazolidinediones promote uptake of glucose into adipose tissue and decrease gluconeogenesis. The role of these compounds in adipogenesis and the evidence presented herein indicates that they are also useful for inhibition of inflammatory cytokine production (for example, TNFα production) and may therefore be used to treat adverse conditions associated with the production of such cytokines. This class of compounds is described, for example, in Kurtz et al., U.S. Pat. No. 5,594,015, and includes such compounds as troglitazone.

The demonstration of a PPARγ-dependent regulatory circuit inhibiting cytokine production is consistent with a general duality between anabolism and inflammation. The inflammatory cytokine TNFα antagonizes the synthesis of PPARγ, blocks adipocyte differentiation, and contributes to insulin resistance. PPARγ agonists in turn promote insulin sensitivity and adipocyte differentiation and block TNFα production. Interestingly, LPS stimulation, which is presumably an acute event, overrides the regulatory influence of PPARγ agonists. Thus it seems likely that the tension between anabolism and inflammation is largely played out in the setting of chronic processes such as parasitemia or autoimmunity.

The discovery that PPARγ agonists inhibit inflammatory cytokine induction indicates that these compounds are useful for treating or preventing adverse conditions associated with inflammatory cytokine responses. Such conditions or diseases include rheumatoid arthritis, inflammatory bowel disease, AIDS, cachexia arising in the setting of neoplasia or chronic infectious disease, and autoimmune diseases with a known or suggested inflammatory component, such as psoriasis and multiple sclerosis. Each of these conditions is known to be associated with the release of one or more inflammatory cytokines and thus would be amenable to PPARγ agonist therapy.

PPARγ Agonist Therapy

For the treatment or prevention of the conditions described herein, PPARγ agonists may be administered in any appropriate formulation and typically are combined with a pharmaceutically-acceptable diluent, carrier, stabilizer, or excipient. Conventional pharmaceutical practice is employed to provide suitable formulations or compositions to administer such compositions to patients. Oral administration is preferred, but any other appropriate route of administration may be employed, for example, intravenous, parenteral, subcutaneous, intramuscular, intracranial, intraorbital, ophthalmic, intraventricular, intracapsular, intraspinal, intracisternal, intraperitoneal, intranasal, or aerosol administration. Therapeutic formulations may be in the form of liquid solutions or suspensions (as, for example, for intravenous administration); for oral administration, formulations may be in the form of tablets or capsules; and for intranasal formulations, in the form of powders, nasal drops, or aerosols.

Methods well known in the art for making formulations are described, for example, in "Remington's Pharmaceutical Sciences," Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes.

If desired, slow release or extended release delivery systems may be utilized. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The PPARγ agonists of the invention are administered at a dosage appropriate to the effect to be achieved and are typically administered in unit dosage form. As noted above, the preferred route of administration for most indications is oral. For treatment of rheumatoid arthritis, intra-articular administration is also appropriate.

An effective quantity of a PPARγ agonist is employed to treat the diseases or conditions described herein. The exact dosage of a compound is dependent, for example, upon the age and weight of the recipient, the route of administration, and the severity and nature of the disease or condition to be treated. In general, the dosage selected should be sufficient to prevent, ameliorate, or treat the disease or condition, or one or more symptoms thereof, without producing significant toxic or undesirable side effects. Preferably, a PPARγ agonist (for example, a thiazolidinedione PPARγ agonist) is administered at a concentration which provides at least a 50% reduction in inflammatory cytokine induction (as measured by inflammatory cytokine concentration) in a monocyte culture assay, for example, the assays described herein. Typically, a PPARγ agonist is administered at a dosage of at least 200 mg and, more preferably, at least 800 mg for oral administration. This dosage is designed to result in a peak concentration of between 5–20 $\mu$M in the bloodstream of the recipient. Administration of a PPARγ agonist may be repeated as necessary and may be combined with other compounds for the treatment of the diseases or conditions described herein.

Preferably, PPARγ agonists are used for the treatment of human patients, but may also be used to treat any other mammal, for example, any pet or domesticated livestock.

Other embodiments are within the claims.

What is claimed is:

1. A method for reducing or preventing inflammatory cytokine production associated with rheumatoid arthritis in a mammal, said method comprising administering to said mammal a thiazolidinedione PPARγ agonist in an amount which is sufficient to produce a 50% inhibition of cytokine production in a mammalian monocyte culture.

2. A method for reducing or preventing inflammatory cytokine production associated with inflammatory bowel disease in a mammal, said method comprising administering to said mammal a therapeutically-effective amount of a thiazolidinedione PPARγ agonist.

3. A method for reducing or preventing inflammatory cytokine production associated with an immunodeficiency syndrome in a mammal, said method comprising administering to said mammal a therapeutically-effective amount of a thiazolidinedione PPARγ agonist.

4. A method for reducing or preventing inflammatory cytokine production associated with multiple sclerosis in a mammal, said method comprising administering to said mammal a therapeutically-effective amount of a thiazolidinedione PPARγ agonist.

5. A method for reducing or preventing inflammatory cytokine production associated with cachexia in a mammal, said method comprising administering to said mammal a therapeutically-effective amount of a thiazolidinedione PPARγ agonist.

6. The method of claim 5, wherein said cachexia results from a neoplasia.

7. The method of claim 5, wherein said cachexia results from a chronic infectious disease.

8. The method of claim 1, 2, 3, 4, or 5, wherein said thiazolidinedione is troglitazone.

9. The method of claim 1, 2, 3, 4, or 5, wherein said cytokine is TNFα, IL-1β, or IL-6.

10. The method of claim 1, 2, 3, 4, or 5, wherein said cytokine is produced by a monocyte.

11. The method of claim 1, 2, 3, 4, or 5, wherein said thiazolidinedione PPARγ agonist is administered orally.

12. The method of claim 2, 3, 4, or 5, wherein said thiazolidinedione PPARγ agonist is administered in an amount which is sufficient to produce a 50% inhibition of cytokine production in a mammalian monocyte culture.

* * * * *

UNITED STATES PATENT AND TRADEMARK OFFICE
CERTIFICATE OF CORRECTION

PATENT NO.   : 5,925,657
DATED        : July 20, 1999
INVENTOR(S)  : Brian Seed and Chengyu Jiang Page 1 of 1

It is certified that error appears in the above-identified patent and that said Letters Patent is hereby corrected as shown below:

<u>Title page,</u>
Item [56], References Cited, OTHER PUBLICATIONS, second Lehmann citation, replace "andti-inflammatory" with -- anti-inflammatory --;

<u>Column 7,</u>
Line 3, replace "intracistemal" with -- intracisternal --.

Signed and Sealed this

Eighteenth Day of June, 2002

Attest:

Attesting Officer

JAMES E. ROGAN
*Director of the United States Patent and Trademark Office*